United States Patent [19]

Ito

[11] 4,439,024

[45] * Mar. 27, 1984

[54] EYE EXAMINING INSTRUMENT WITH VARIABLE INTENSITY OF ILLUMINATION LIGHT

[75] Inventor: Yuji Ito, Chigasaki, Japan

[73] Assignee: Canon Kabushiki Kaisha, Tokyo, Japan

[*] Notice: The portion of the term of this patent subsequent to Jan. 27, 1998 has been disclaimed.

[21] Appl. No.: 32,683

[22] Filed: Apr. 23, 1979

[30] Foreign Application Priority Data

Apr. 25, 1978 [JP] Japan .................................. 53-49025

[51] Int. Cl.³ .......................... A61B 3/14; G03B 29/00
[52] U.S. Cl. ...................................... 351/207; 354/62
[58] Field of Search ............... 351/7, 16; 354/62, 201, 354/221

[56] References Cited

U.S. PATENT DOCUMENTS 4,068,932  1/1978  Ohta et al. ............................. 351/7
4,102,563  7/1978  Matsumura et al. .................. 351/7

*Primary Examiner*—John K. Corbin
*Assistant Examiner*—Rodney B. Bovernick
*Attorney, Agent, or Firm*—Toren, McGeady and Stanger

[57] ABSTRACT

In the disclosed eye examining instrument, an eye inspection system forms a first optical path and an eye illuminating system forms a second optical path which begins outside the first optical path and then extends along the optical axis of the first optical path near the eye. A shading member in the optical path of the illuminating member is substantially conjugate with the pupil of the eye and cooperates with variable limiting means that vary the shading. In one embodiment, the variable limiting means is a second shading member movable toward and away from the first shading member along the optical path of the illuminating system and conjugate with an interior portion of the eye so as selectively to block out portions of the unshaded light reaching the eye fundus.

26 Claims, 8 Drawing Figures

EYE EXAMINING INSTRUMENT WITH VARIABLE INTENSITY OF ILLUMINATION LIGHT

BACKGROUND OF THE INVENTION

The present invention relates to an eye examining instrument, particularly for examining and photographing the interior of an eye.

In order to use eye examining instruments, such as eye fundus cameras, for mass examinations to prevent adult diseases, the picture angles of these instruments have been made wider and wider. This permits inspection and photography of a large portion of the eye at one time so that a number of persons can be examined in a short period. However, if damage or disease is suspected from the first examination or photographic inspection, an eye fundus camera is still needed for producing a highly magnified picture.

Eye fundus cameras operate by illuminating an eye fundus when the latter is coaxial with the camera's objective lens. Under these circumstances, a part of the illuminating light is reflected by the cornea of the eye and strikes the film. This causes undesirable flare on the film.

In a known practical large eye fundus camera an apertured mirror is placed between the objective lens and the image forming lens. A black spot is provided at a position conjugate with the cornea between the mirror and the light source, so that its' image is formed on the cornea. The eye fundus illumination light is permitted in at the edge of the black spot's shadow. The light reflected on the eye fundus passes through the shadow formed on the cornea so as to separate the illumination light from the reflected light. Thus the reflected light passes through the aperture in the mirror, and is led to the image forming lens. On the other hand, part of the illumination light is reflected on the objective lens. The latter is shaped such that the light reflected on it is condensed on the black spot provided in the lens. However, it is difficult and time consuming to manufacture an objective lens with a special shape, and its picture angle as well as its efficiency are restricted. In accordance with the Japanese Patent Publication No. Sho 44-8406, a black spot is provided between the light source and the aperture mirror so as to interrupt the light beam reflected on the objective lens surface in order to avoid the above mentioned difficulty.

Another problem occurs when the picture field angle of the eye fundus camera is enlarged from 30° to 45°. That is, when the picture field angle is narrow the image of the black spot formed on the cornea has a long tail directed toward the eye fundus so that the front and the rear surfaces of the lens lie in this shadow. Thus no reflection take place. When, however, the incident angle of the illumination light becomes larger due to the increase of the field angle, the shadow of the black spot becomes shorter such that a part of the illumination light is reflected on the surface of the lens so that a flare occurs on the picture. In accordance with U.S. Pat. No. 3,851,954, a black spot is provided between the light source and the aperture mirror so as to eliminate the light reflected on the lens.

Further, in accordance with U.S. Pat. No. 4,102,563, other undesirable light due to the lens is eliminated. This undesirable light arises because, the liquid in the lens is not always transparent so that the illuminating light is dispersed. Further, the illuminating light is dispersed on the rear surface of the lens, so that a flare appears like mist over a wider range than that due to the reflected light which appears comparatively clear. As the counter-measure against the above, the range on the lens through which the photographic light (light beam striking the film through the objective lens, the aperture in the mirror and the image forming lens) passes is covered with a black spot.

When a black spot is provided, the illumination light incident on the eye fundus is decreased by the amount of light interrupted with the image of the spot. However, for an eye fundus camera of a non pupil dilation system with focus adjustment by means of infrared light, no pupil dilation means is used, and a picture is taken in a natural state with a flash. However, in extreme cases such as that of an old man whose pupil can not be dilated sufficiently, even in a dark chamber the amount of the photographic light is often too small. Consequently, an under-exposure occurs in an instrument whose flash intensity is predetermined.

Further, in the case of the fluorescent fundus angiography an exciter filter is provided in the illumination light, while a barrier filter is provided in the photographic light. Thus the light transmittance is substantially decreased, and it becomes necessary to increase the retina illumination more than in ordinary photography.

SUMMARY OF THE INVENTION

A purpose of the present invention is to eliminate undesirable light.

Another purpose of the present invention is to make the amount of illumination from the object variable independent from that of the light source.

Still another purpose of the present invention is to increase the illumination intensity of the object at the narrow picture angle when the object is observed or photographed with variable magnification.

Yet another purpose of the present invention is to eliminate the undesirable light produced by areas other than those observed or photographed.

DESCRIPTION OF THE PREFERRED EMBODIMENTS

Figure 1:
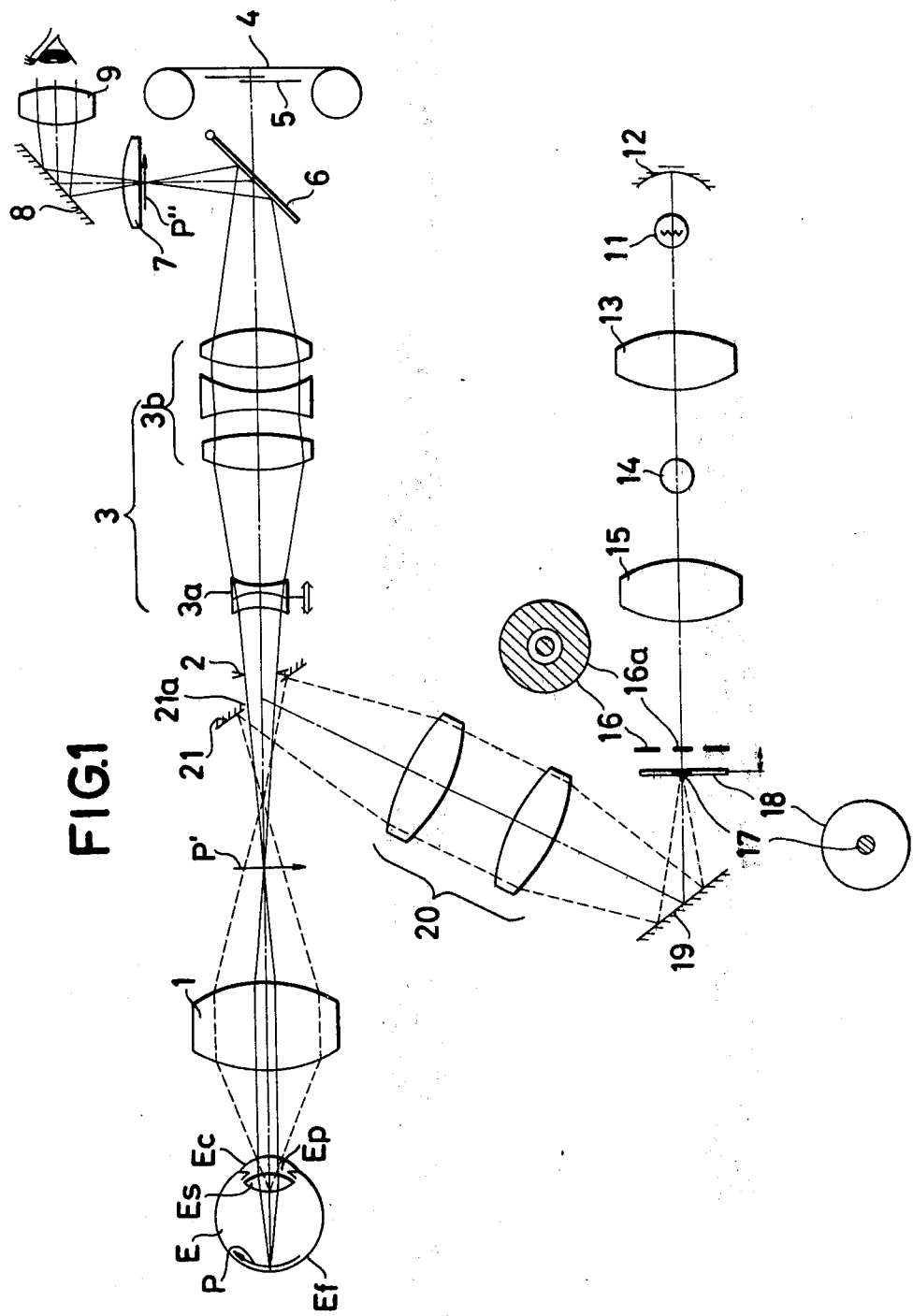
FIG. 1 shows an embodiment of the present invention in section.

In the drawings, an eye E to be inspected includes an eye fundus Ef, a cornea Ec, a pupil Ep, and a lens Es. The photographic system for photographing the eye includes an objective lens 1, a diaphragm 2, an image forming lens 3, a film 4, and a shutter 5.

The diaphragm may be a mirror with a hole, and is nearly conjugate with the pupil or the cornea. A negative lens group 3a in the image forming lens 3 is movable for focus adjustment, while a positive lens group 3b is stationary. Instead of moving the lens 3b the distance between the imageforming lens and the film may be changed to focus properly.

A mirror 6 (to be lifted) is provided at an angle between the image forming lens 3 and the shutter 5 during observation so as to reflect the light beam to the finder and withdraw it from the photographic light path. A field lens 7 is provided almost conjugate with the film with reference to the mirror to be lifted. A mirror 8 redirects the optical path to an eye piece lens 9.

Light from a light source 11, such as tungsten light, is reflected by a concave mirror 12 through a first condenser lens 13 passed a photographic light source such as a flash and through a second condenser lens 15. A ring slit disc or plate 16 forms a circular opening with a light shading range 16a at its center that forms a light passage range.

The observation light source 11 and the photographic-light source 14 are conjugate with each other with reference to the first condenser lens 13, while the photographic light source 14 and the ring slit plate 16 are conjugate with each other with reference to the second condenser lens 15.

A light shading black spot 17 is cemented onto a transparent disc 18. Suitable means outside the housing (not shown) can move the disc 18 and the black spot 17 along the optical axis of the lenses 13 and 15. A mirror 19 changes the optical path and a relay lens or relay lens group 20 directs the light to a mirror 20 having a central opening 21a and positioned where the optical path of the photographic system crosses that of the relay lens group so as to separate the photographic from the illuminating light. The members from the concave mirror 12 to the mirror 21, including the objective lens 1, constitute the illumination system.

The ring slit plate 16 and the pupil Ep of the eye to be inspected or the cornea Ec are conjugate to each other with reference to the mirror 19, the relay lens group 20, the surface of the mirror 21 and the objective lens 1. Further, the black spot 17, when furthest from the ring slit, is conjugate, to the eye fundus side surface of the lens Es with respect to the mirror 19, the relay lens group 20, the mirror 21 and the objective lens 1.

In the above mentioned structure, the beam from the observation light source 11 is made to converge on the ring slit disc 16 by passing it through first and the second condenser lenses 13 and 15 so as to illuminate the disc 16. The opening of the illuminated ring slit disc 16 serves as a ring-shaped secondary light source, so that the light beam passing through it is reflected on the mirror 19, condensed by the relay lens group 20 and form the image of the secondary light source on the mirror 21. This reflected image of the secondary light source then reaches pupil Ep through the objective lens 1 and illuminates the eye fundus Ef evenly over the wide range. A random reflection also occurs at the illuminated eye fundus P so that a part of the reflected light beam passing through the diaphragm passes through the central part of the image of the secondary light source, namely the image of the light shading range 16a. This light then goes out of the eye to be inspected and reaches the objective lens 1, so as to form an intermediate image. Then, the light beam passes through the opening 21 at the center of the mirror 21a, and the diaphragm 2, reaches the image forming lens 3 where it is condensed, and is reflected on the mirror 6 so as to form an image P″ of the eye fundus in the neighborhood of the field lens 7. Thus the image P″ of the eye fundus appears through the eye piece lens 9.

When the view field makes it too dark to observe the image of the eye fundus, the plane disc 18 may be moved toward the ring slit disc 16 in order to increase the amount of light, i.e., the illumination. The reason for this increase is explained with respect to FIGS. 2 and 3.

Figure 2:
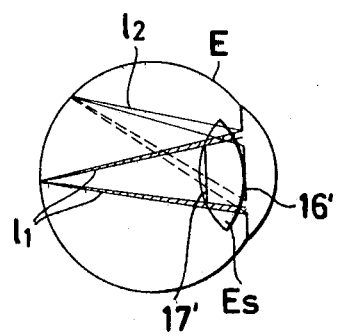
FIGS. 2 and 3 show the interior of the eye to be inspected in section.
Figure 3:
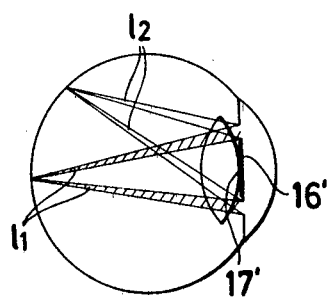

FIGS. 2 and 3 show the optical efficiency in the eye to be inspected. An image of the light shading range of the ring slit disc 16 is represented by numeral 16′, while an image of the black spot 17 is represented by numeral 17′. The illuminating beam is permitted through the opening of the image 16′ of the light shading range. Far the sake of simplicity the illumination beam $l_1$ directed to the center is designated by slanting lines, while the light beam $l_2$ directed to the periphery is designated by dots. As is clear from FIG. 2, the image 17′ of the black spot 17 intercepts parts of the light beam $l_2$ directed toward the periphery and that $l_1$ directed toward the center. When then the light shading black spot 17 is brought into contact with the ring slit plate 16, the image 17′ of the black spot coincides with the image 16′ of the light shading range of the ring slit disc 16. Thus, as in FIG. 3, the light along the periphery reaches the eye fundus so as to illuminate it. Although only a section is shown in the drawing, the situation is identical for all 360° so that the light amount is uniformly increased.

Consequently, lighting of the eye fundus can be adjusted both for wide angle pictures and narrow angle pictures with simple optical means.

For the present invention, the black spot 17 is brought into contact with the ring slit disc 16 so as to obtain a bright view field and accurate focussing. The light shading black spot 17 is brought into the initial position, the observation light source 11 is extinguished while the photographic light source 14 is lit up, the mirror 6 is lifted while the shutter 5 is opened and the film 4 is exposed to the light reflected from the eye fundus. The geometry of the light emitted from the photographic source is almost the same as that of the observation light source.

Further, when, in the case of the first embodiment, the positive lens group 3b of the image forming lens is changed or a magnification increasing lens (not shown) is inserted between the fixed positive lens group 3b and the mirror 6, the magnification factor of the photographing system can be varied. Further, when behind the mirror 21, a zoom lens (not shown) is provided, the magnification can be changed continuously.

Figure 4:
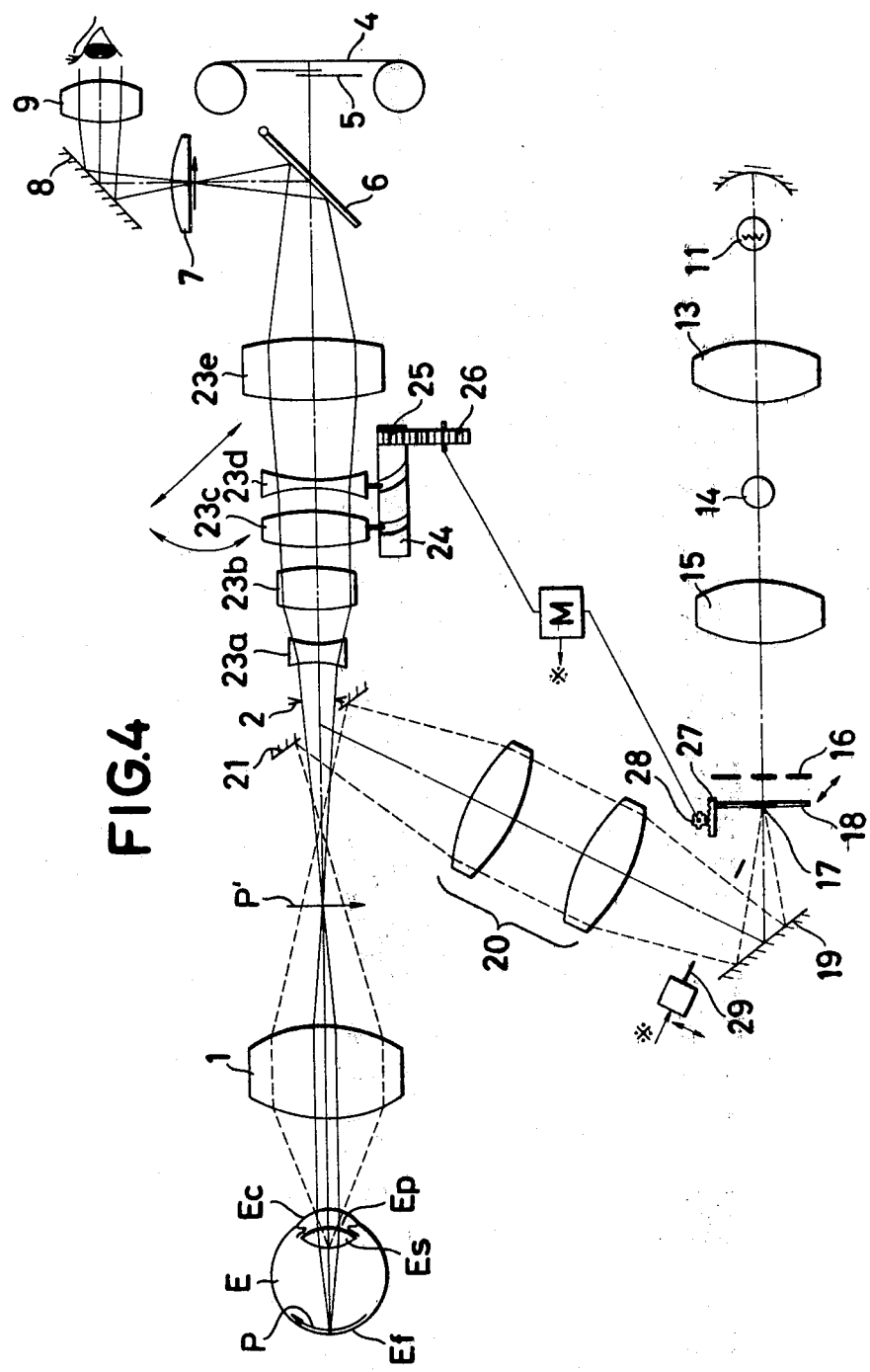
FIG. 4 illustrates another embodiment of the present invention in section.

In FIG. 4, members corresponding to those in FIG. 1 are designated with like reference numerals. In FIG. 4, a zoom lens is composed of a negative focusing lens group 23a, a positive stationary lens group 23b, a positive compensation lens group 23c, a variator lens group 23d, and a stationary lens group 23e. The lens groups 23c and 23d move simultaneously but independently to produce a zooming effect so that both narrow and wide angle photography of the eye fundus is possible. A cam tube 24 includes cam grooves which engage pins secured on the lens groups. The pins are also guided by straight grooves (not shown) extending in the direction of the optical axis between the member 24 and the lenses 23c, 23d.

A gear 25 secured on the cam tube 24 engages the driving pinion 26. The gear 25 rotates the cam tube 24 so that the lens groups 23c and 23d move along the predetermined cam curves.

An adjusting mechanism M controls the variation of the magnification factor and the amount of the movement of the black spot 17. The permeable disc 18 holding the black spot 17 is secured on a rack 27 engaged with a pinion 28. Adjusting mechanism M determines the amount of rotation of pinion 26 so that in wide angle photography the black spot 17 is positioned from the ring slit disc 16 so that the undesirable light beam is prevented from reaching the lens. When the photographic system is of a narrow angle, the transferent plane disc 18 is in contact with the ring slit disc 16. Consequently, when one zooms into a wide angle, the image 17' of the black spot is formed in or on the rear surface of the lens on the other hand, when the photographing optics are of a narrow angle the image 17' of the black spot almost coincides with the image 16' of the light shading range so the decrease of the amount of illumination is prevented.

A diaphragm such as an iris pupil whose opening diameter can be varied freely is represented by numerals 29. The plane on which the diaphragm 29 is provided is operatively engaged with the focusing lens group 23 so as to be conjugate with the eye fundus Ef with reference to the relay lens group 20, the mirror 21 and the objective lens 1 and movable along the optical axis. Consequently, when the diaphragm 29 is narrowed, the range of the eye fundus to be illuminated is made smaller.

To drive the diaphragm 29, it is convenient to operatively engage it with the rotation of the pinion 26. When the photographic optics are of a wide angle type the diaphragm diameter is its largest, while in narrow angle photographic optics the diaphragm diameter is its smallest and the inside edge of the image of the diaphragm coincide with the range to be photographed.

Figure 5:
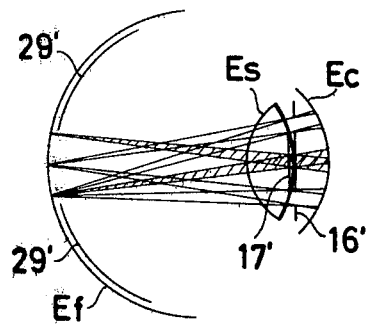
FIGS. 5, 6 and 7 each show the interior of the eye to be inspected in section.
Figure 6:
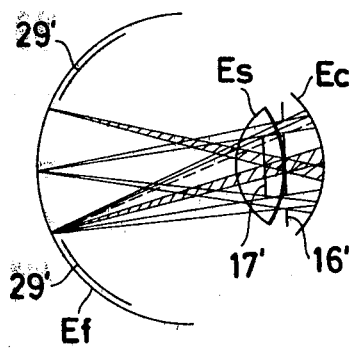
Figure 8:
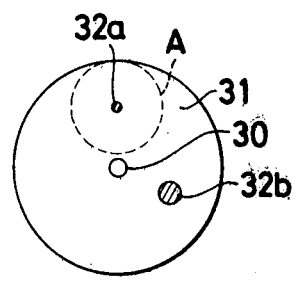
FIG. 8 illustrates a member composed of a permeable disc with a plural number of black spots in plane view.
Figure 7:
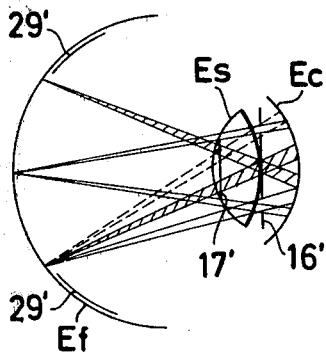

FIGS. 5, 6 and 7 show the inside of the eye to be inspected for narrow angle, middle angle and wide angle photograph respectively. Again, numeral 16' represents the image of the light shading range of the ring slit disc 16, 17' represents the image of the black spot and 29', the image of the diaphragm. Further, the blank light beam represents the illumination light beam, while that with slanted lines represents the photographic light beam. In accordance with the change of picture angle the image 17' of the black spot moves so that the photographic light beam never overlaps the illumination beam in the lens. Thus even if the illumination beam is reflected and dispersed in the lens, the photographic beam is never disturbed.

In the present embodiment, the picture angle of the eye fundus illumination optics is determined so as always to illuminate a predetermined range. In case the magnification factor can be changed the picture angle is always set at the wide angle side, so that at the narrow angle side a larger range than what is photographed actually. Further, in the case of a concave plane such as eye fundus the light reflected and dispersed on the periphery is apt to cause ghost or flare. In the present embodiment the circumference of the range to be photographed is shaded from the light by the image 29' of the diaphragm so that such difficulties can be eliminated. As is clear from FIGS. 5 to 7, the range to be shaded by means of the image 29' of the diaphragm varies in accordance with the change of the picture angle.

The movement of the image 17' of the black spot can be approximated by a change of the area of the lens projected in the direction of the eye fundus. Similarly, step movement of the black spot can be obtained when a permeable disc 31 rotatable around a shaft 30 is provided at a position conjugate toward the eye fundus with reference to the lens. Black spots 32a, 32b of different size are provided on the disc 31, which is then rotated in the range A of the illumination light beam so as to bring the spots to position coincident to the optical axis.

The aforementioned embodiments relate to the conventional eye fundus camera. It goes without saying that the present invention can be applied to the eye fundus camera of a non-dilation pupil type. One advantage of the present invention lies in the fact that illumination can be adjusted without electrical means. In accordance with the present invention the photographic and observation light sources can be controlled together from one position. Further, generally speaking, if the magnification factor of the photographing system is variable a shortage of the light is apt to occur in the high magnification range, while in case the light shading means is stationary a part of the illumination light is interrupted at the side of narrow angle. However, in accordance with the present invention this inconvenience, namely the shortage of light amount, can be effectively compensated.

What is claimed is:

1. An eye examining instrument comprising:
   an eye inspecting system for inspecting an eye to be examined;
   an illuminating system arranged to direct light into the eye inspection system and toward the eye to be examined and forming an optical path, said illuminating system having a first light shading member at a position conjugate with the anterior part of the eye to be inspected in the optical path and a second light shading member, for eliminating undesirable light due to the lens of the eye to be inspected in the optical path so as to alter the amount of the illuminating light at the eye to be examined in cooperation with the first light shading member;
   at least one of said shading members being variable relative to the other.

2. An eye examining instrument in accordance with claim 1, wherein the second light shading member includes an opaque element movable along the optical path of the illuminating system.

3. An eye examining instrument in accordance with claim 2, wherein the opaque element is movable between the first light shading member and a position conjugate with the retina side of the lens of the eye to be inspected.

4. An eye examining instrument in accordance with claim 1, wherein the second light shading member is arranged for eliminating undesirable light due to a lens of an eye being examined and includes control means for varying dimensions of an opaque axial area.

5. An eye examining instrument in accordance with claim 4, wherein the control means includes a plurality of black spots of different sizes.

6. An eye examining instrument in accordance with claim 4, further comprising magnification varying means coupled with the second light shading member to change the picture angle.

7. An eye examining instrument in accordance with claim 6, wherein the magnification varying means includes movable lenses movable along the optical path of the eye inspecting system and drive means for driving the movable lenses.

8. An eye examining instrument in accordance with claim 1, wherein the illuminating system further includes variable aperture means having a variable aperture at a position substantially conjugate with the fundus of the eye to be inspected.

9. An eye examining instrument in accordance with claim 1, wherein the eye inspection system further includes magnification varying means for varying the picture angle, and the illumination system further includes variable aperture means connected to the magnification varying means having a variable aperture at a position substantial at the eye fundus to be inspected.

10. An eye examining instrument in accordance with claim 1, wherein the eye inspecting system includes, in sequence, a front optical arrangement, aperture means for forming an aperture, an image forming lens, beam direction selecting means, image recording means and a finding apparatus optically coupled to the beam direction selecting means; and the illuminating system includes, in sequence, at least one beam source, a condenser lens arrangement; a relay lens arrangement, a beam reflector, and the front optical means; the first and the second light shading member being provided between the light source and the beam reflector.

11. An eye examining instrument in accordance with claim 10, wherein the first light shading member includes an opaque spot provided on the optical axis of the illuminating system and an aperture stop.

12. An eye examining instrument in accordance with claim 10, wherein the second light shading member includes an opaque spot movably mounted along the optical axis of the illuminating system.

13. An eye examining instrument in accordance with claim 10, wherein the second light shading member includes an opaque spot dismountably mounted on the optical axis of the illuminating system.

14. An eye examining instrument comprising an inspection system including, in sequence along an optical path, an optical apparatus including front optical means, aperture means, and an image forming lens; and an illuminating apparatus forming an optical axis, and including at least one light source for producing an illuminating light flux and light transmitting means on the axis to illuminate the eye to be inspected through the front optical means and an opaque element for eliminating a part of the illuminating light flux, said element being movable along the optical axis of the illuminating apparatus to vary the intensity of the light incident on the eye fundus, and conjugate to a front portion of the eye being examined within its moving range.

15. An eye examining apparatus comprising: an inspection system including, in sequence along an optical path, an optical apparatus including front optical means, aperture means and an image forming lens; and an illuminating apparatus including at least one beam source and beam transmitting means forming an optical axis to illuminate the eye to be examined through the front optical means, and an opaque element on the axis dismountably mounted on the optical axis of the illuminating apparatus to provide a change in the light intensity on the eye fundus and arranged to be conjugate to a front portion of an eye being examined.

16. An eye examining apparatus comprising:
an optical apparatus including, in sequence, front optical means, aperture means and an image forming lens, all arranged along an examining path;
an illuminating apparatus forming an illuminating path that in part passes through the front optical means along the examining path including at least one beam source and beam transmitting means in the optical path to illuminate the eye to be inspected through the front optical means; and
a diaphragm with a variable opening provided at a position conjugate with the eye fundus to be inspected in the optical path of the illuminating apparatus.

17. An eye examining instrument in accordance with claim 16, wherein the image forming lens includes lens means for causing a change of focal length, the opening of the diaphragm being arranged for varying in association with the focal length of the image forming lens.

18. An eye examining apparatus in accordance with claim 16, wherein said diaphragm is movable along the optical axis of the illuminating apparatus.

19. An eye examining apparatus comprising:
photographing means for photographing the fundus of an eye to be inspected, said photographing means including means for focusing said photographing means and optical means for changing the angle of the view of said photographing means;
viewing means connected with said photographing means for viewing the fundus of the eye;
illuminating means for illuminating the fundus of the eye and forming an optical path; and
shading means in the path of the illuminating means for forming a peripherally shaded area on the eye fundus and an interiorly shaded area on the lens surface of the eye and for varying the size of the peripherally shaded area on the eye fundus.

20. An eye examining apparatus comprising:
photographing means for photographing the fundus of an eye to be inspected, said photographing means including means for focusing said photographing means and optical means for changing the angle of the view of said photographing means;
viewing means connected with said photographing means for viewing the fundus of the eye;
illuminating means for illuminating the fundus of the eye and forming an optical path;
aperture means for shading a part of the fundus of the eye in the optical path of said illuminating means for varying a sectional area of the optical path of said illuminating means;
said aperture means being engaged with said optical means, the variation of the sectional area being arranged for taking place in association with the variation in the view angle of the photographing means.

21. An eye examining apparatus comprising:
photographing means for photographing the fundus of an eye to be inspected, said photographing means including means for focusing said photographing means and optical means for changing the angle of the view of said photographing means;
viewing means connected with said photographing means for viewing the fundus of the eye;
illuminating means for illuminating the fundus of the eye and forming an optical path;
aperture means for shading a part of the fundus of the eye in the optical path of said illuminating means for varying a sectional area of the optical path of said illuminating means;
said aperture means engaging said focusing means and being movable along the optical path of the illuminating means.

22. An eye examining apparatus comprising:
photographing means for photographing the fundus of an eye to be inspected;

said photographing means including in order objective means, an aperture, and optical means for changing the angle of the view of said photographing means;

viewing means connected with said photographing means for viewing the fundus of the eye;

illuminating means for illuminating the fundus of the eye and forming an optical path;

first light shading means for eliminating reflections due to the cornea of the eye in the optical path of said illuminating means; and second light shading means for eliminating undesirable light due to the lens of the eye and for varying dimension of an axial shading area in the optical path of said illuminating means.

23. An eye examining apparatus in accordance with claim 22, wherein said second light shading means is engaged with said optical means.

24. An eye examining apparatus according to claim 20, wherein said aperture means is arranged so that the sectional area becomes smallest at the narrowest angle of view of the photographing means so as to eliminate undesirable light due to the eye fundus.

25. An eye examining instrument comprising an inspection system including, in sequence along an optical path, an optical apparatus including front optical means, aperture means, and an image forming lens; and an illuminating apparatus forming an optical axis, and including at least one light source for producing an illuminating light flux and light transmitting means on the axis to illuminate the eye to be inspected through the front optical means and an opaque element for eliminating a part of the illuminating light flux, said element being movable along the optical axis of the illuminating apparatus, and conjugate to a front portion of the eye being examined within its moving range, the image forming lens including means for causing a change of focal length, the opening of the diaphragm being arranged for varying in association with the focal length of the image forming lens.

26. An eye examining apparatus comprising: an inspection system including, in sequence along an optical path, an optical apparatus including front optical means, aperture means and an image forming lens; and an illuminating apparatus including at least one beam source and beam transmitting means forming an optical axis to illuminate the eye to be examined through the front optical means, and an opaque element on the axis dismountably mounted on the optical axis of the illuminating apparatus and arranged to be conjugate to a front portion of an eye being examined, the image forming lens including means for causing a change of focal length, the opening of the diaphragm being arranged for varying in association with the focal length of the image forming lens.

* * * * *